(12) United States Patent
Wikström et al.

(10) Patent No.: US 6,291,494 B1
(45) Date of Patent: Sep. 18, 2001

(54) 2-AMINOTHIAZOL-FUSED 2-AMINOINDANS AND 2-AMINOTETRALINS AND THEIR USE

(76) Inventors: Håkan Vilhelm Wikström, Elschotlaan 32, Groningen, NL-9721 WN (NL); Per Erik Andrén, Floragatan 17F, Uppsala, SE-75218; Per Arvid Emil Carlsson, Torild Wulffsg. 50, Göteborg, SE-41319, both of (SE); Durk Dijkstra, De Meidoorn 26, NL-9781 VP Bedum (NL); Lars Gunne, Stackvägen 24, SE-75647 Uppsala (SE); Leonard Alexander Van Vliet, Bedumerstraat 155A, NL-9716 BH Groningen (NL)

( * ) Notice: Subject to any disclaimer, the term of this patent is extended or adjusted under 35 U.S.C. 154(b) by 0 days.

(21) Appl. No.: 09/720,911
(22) PCT Filed: Jul. 1, 1999
(86) PCT No.: PCT/SE99/01197
  § 371 Date: Feb. 9, 2001
  § 102(e) Date: Feb. 9, 2001
(87) PCT Pub. No.: WO00/01680
  PCT Pub. Date: Jan. 13, 2000

(30) Foreign Application Priority Data

Jul. 1, 1998 (SE) ..................... 9802360

(51) Int. Cl.$^7$ ............... A61K 31/428; C07D 277/60; C07D 277/82
(52) U.S. Cl. ............................. 514/366; 548/150
(58) Field of Search ............... 548/150; 514/366

(56) References Cited

U.S. PATENT DOCUMENTS 2,055,609  9/1936  Lubs et al. ............... 260/44
4,826,860  5/1989  Johnson et al. ............... 514/367

FOREIGN PATENT DOCUMENTS 0186087  7/1986  (EP) .

OTHER PUBLICATIONS

"Synthesis and Biological Activities of New 1,4–Benzothiazine Derivatives," by Kajino et al., Chem. Pharm. Bull., vol. 39, No. 11, 1991, pp. 2888–2895.

Primary Examiner—Laura L. Stockton
(74) Attorney, Agent, or Firm—McDermott, Will & Emery

(57) ABSTRACT

The invention relates to 2-aminothiazol-fused 2-aminoindans and 2-aminotetralins having general formula (1): wherein $R_1$ and $R_2$, which may be identical or different, are selected from the group consisting of a hydrogen atom, alkyl or haloalkyl groups of 1 to 7 carbon atoms, (alkyl) cycloalkyl groups of 3 to 7 carbon atoms, alkenyl or alkynyl groups of 3 to 6 carbon atoms, arylalkyl having 1 to 3 carbon atoms in the alkyl moiety, while the aryl nucleus may be substituted; and n and m are 1 or 2; and the enantiomers and the acid addition salts thereof, pharmaceutical compositions containing them and their use in the preparation of medicaments having an effect on the dopaminergic system of the central nervous system and/or the circulation.

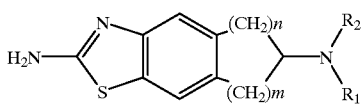

18 Claims, No Drawings

2-AMINOTHIAZOL-FUSED 2-AMINOINDANS AND 2-AMINOTETRALINS AND THEIR USE

This application is a 371 of PCT/SE99/01197 filed Jul. 1, 1999.

DESCRIPTION

1. Technical Field

The present invention relates to new 2-amino-thiazol-fused 2-aminoindans and 2-aminotetralins and their use. More particularly, the present invention relates to (basic)N-substituted and (basic)-N,N-disubstituted derivatives of 2,6-di-amino-thiazolo[4,5-f]indan, 2,7-di-amino-thiazolo[4,5-g]-tetralin and 2,7-di-amino-thiazolo[5,4-g]-tetralin having pharmacologically valuable properties, acid addition salts thereof, pharmaceutical compositions containing them and their use in the preparation of medicaments.

2. Background Art

Numerous tetrahydro-benzothiazoles are known from the literature. Thus, U.S. Pat. No. 4,337,343 describes 4,5,6,7-tetrahydro-benzothiazoles which are substituted in the 2 position by a hydrogen atom or an alkyl group and in the 4, 5 or 6 position by an alkylaminoalkyl group and have an effect on the circulation, U.S. Pat. No. 4,208,420 describes 4,5,6,7-tetrahydro-benzothiazoles which are substituted in the 2 position by a hydrogen atom or an alkyl group and the 4,5 or 6 position by an alkylamino group and have, inter alia, a stimulatory effect on the sympathetic nervous system and act as regulators of the cerebral vascular system, and DE-A-2.136.233 describes 4,5,6,7-tetrahydro-benzothiazoles ureido or thioureido group and have virustatic properties. optionally substituted ureido of thioureido group and have virustatic properties.

The tetrahydrobenzothiazole Pramipexol® (Mirapex) is presently marketed as a drug against Parkinson's disease (pat. appl. Griss et al., EP 186087 A1 860702; See also Schneider and Mireau, JMC 1987, 30, 494–498).

However, 2-aminothiazole-fused 2-aminoindans and 2-aminoteralins, of the type claimed in this invention (Formula 1 below), have not been described before.

A CAS ONLINE search in the registry file on Jun. 9, 1998 gave no hits on the following truncated structures, thus supporting the fact that the compounds claimed in Formula 1 below are new. Compounds searched and not found in CAS ONLINE (substructure searches; in these searches the indane and tetralin ring system hydrogens were specified and only the two "free site" substituents were allowed to be any substituent possible in CAS ONLINE):

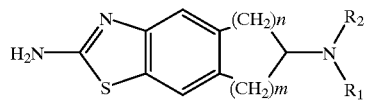

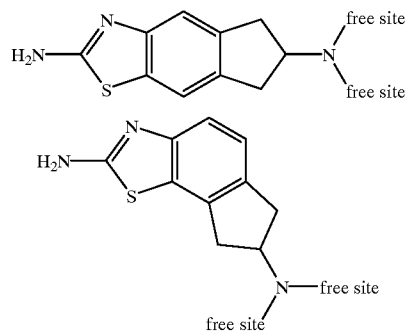

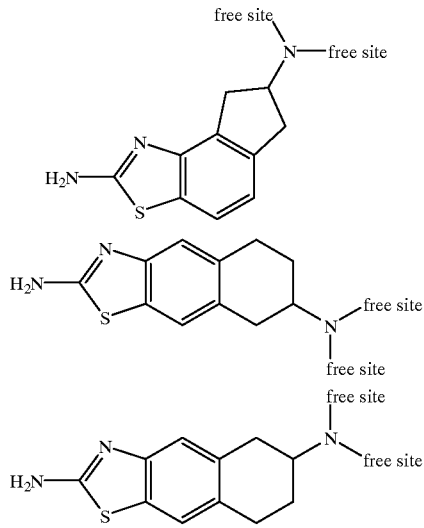

SUMMARY OF THE INVENTION

In one aspect the subject invention is related to new 2-aminothiazol-fused 2-aminoindans and 2-aminotetralins of the general formula (Formula 1):

$$\text{H}_2\text{N} - \underset{S}{\overset{N}{\diagup}} \diagdown \overset{(CH_2)n}{\underset{(CH_2)m}{\diagdown}} \diagup N \diagdown \overset{R_2}{\underset{R_1}{\diagup}}$$

wherein $R_1$ and $R_2$, which may be identical or different are selected from the group consisting of a hydrogen atom, alkyl or haloalkyl groups of 1 to 7 carbon atoms, (alkyl)cycloalkyl groups of 3 to 7 carbon atoms, alkenyl or alkynyl groups of 3 to 6 carbon atoms, arylalkyl groups having 1 to 3 carbon atoms in the alkyl moiety, whilst the aryl nucleus may be substituted (e.g. by fluorine, chlorine or bromine atoms or a sulfonyloxy (e.g. a triflate)group), and n and m are both 1 (2-aminothiazol-fused 2-aminoindans; Formula 1a):

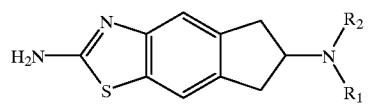

or n is 2 and m is 1 (2-aminothiazol-fused 2-aminotetralins; Formula 1b):

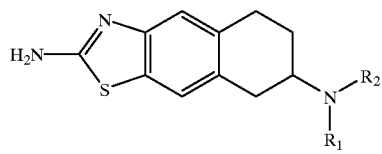

or n is 1 and m is 2 (2-aminothiazol-fused 2-aminotetralins; Formula 1c):

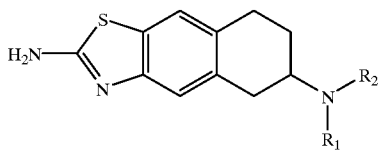

and the enantiomers ant the acid addition salts thereof, particularly the physiologically acceptable acid addition salts thereof with inorganic or organic acids.

Compounds of general Formula 1 have valuable pharmacological properties, particularly an effect on the dopaminergic system of the central nervous system and/or the circulation.

According to another aspect, the present invention relates to pharmaceutical compositions containing as an active substance a compound of Formula 1 or a physiologically acceptable acid addition salt thereof, optionally together with one or more inert carriers and/or diluents.

According to a further aspect, the present invention relates to the use of a compound of Formula 1 or a physiologically acceptable acid addition salt thereof for preparing a drug having an effect on the dopaminergic system of the central nervous system and/or the circulation, e.g. for treating dopamine receptor related central nervous neuro-psychiatric diseases, circulatory disorders, schizophrenia, Parkinson's disease, Parkinsonism or drug abuse, in particular alcohol and/or cocaine abuse.

According to a still further aspect, the present invention relates to a process for preparing a pharmaceutical composition characterized in that a compound of Formula 1 or a physiologically acceptable salt thereof is incorporated in one or more inert carriers and/or diluents by a non-chemical method.

DETAILED DESCRIPTION OF THE INVENTION

The compounds of this invention are represented by Formula 1 or a pharmaceutically acceptable salt thereof as shown above. The compounds may be used in a method for treating mammals, especially humans, suffering from dopamine generated central nervous system disorders (e.g. schizophrenia, Parkinson's disease, Tourette's Syndrome, MBD, hyperprolactinemia and drug abuse (e.g. abuse of alcohol or cocaine)) by administering a therapeutically effective amount of a Formula 1 compound.

In the structural Formula 1, the carbon content of various hydrocarbon-containing moieties is indicated by expressing that the moiety contains "i to j carbon atoms". Thus, a "1 to 7 carbon atoms" alkyl refers to straight and branched alkyls of one to seven carbon atoms, inclusive, including isomers thereof such as methyl, ethyl, propyl and isopropyl.

Cycloalkyl are three to seven carbon atoms such as cyclopropyl, cyclobutyl, cyclopentyl, cyclohexyl and cycloheptyl.

The term "halogen" includes fluoro, chloro, bromo and iodo.

As examples of the definitions of the group —$NR_1R_2$ this group represents an amino, methyl-amino, ethylamino, n-propylamino, isopropylamino, n-butylamino, isobutylamino, tert-butylamino, n-pentylamino, isoamylamino, n-hexylamino, n-heptylamino, dimethylamino, di-ethylamino, di-n-propylamino, di-n-butylamino, methyl-ethylamino, methyl-n-propylamino, methyl-isopropylamino, ethyl-isopropylamino, 2,2,2-trifluoro-ethylamino, 3,3,3-trifluoro-propylamino, 2-fluoro-ethylamino, 3-fluoro-propylamino, allylamino, buten-2-ylamino, hexen-2-ylamino, diallylamino, N-methyl-allylamino, N-ethyl-allylamino, N-n-propyl-allylamino, N-n-butyl-allylamino, propargylamino, buten-2-ylamino, hexen-2-ylamino, dipropargylamino, N-methyl-propargylamino, N-ethyl-propargylamino, cyclopropylamino, cyclobutylamino, cyclo-pentylamino, cyclohexylamino, cycloheptylamino, N-methyl-cyclohexylamino, N-ethyl-cyclohexylamino, benzylamino, chlorobenzylamino, bromobenzylamino, 1-phenylethylamino, 2-phenylethylamino, 2-phenyl-n-propylamino, 3-phenyl-n-propylamino, N-methyl-benzylamino, N-ethyl-benzylamino, N-ethyl-p-chlorobenzylamino, N-ethyl-2-phenylethylamino, N-allyl-benzylamino, N-allyl-p-chlorobenzylamino, n-propyl-phenylethylamino, n-propyl-2-thienylethylamino, n-propyl-3-thienylethylamino group.

As further examples of the group "arylalkyl", this group represents an alkyl part of 1–3 carbon atoms, where the aryl part can be taken from (substituted) phenyl, 1- or 2-naphtyl, 2-, 3- or 4 -pyridyl, 2- or 3-thienyl, 2- or 3-furanoyl, 2- or 4-imidazolyl and 1-imidazolin-2-one, the three last given as structural formulas for clarity:

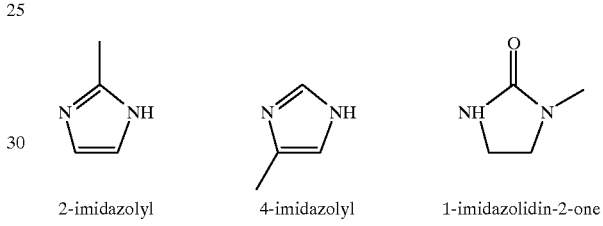

2-imidazolyl    4-imidazolyl    1-imidazolidin-2-one

Pharmaceutically acceptable salts means salts useful for administering the compounds of this invention or useful forms the compounds may take in vitro and in vivo and include the acid addition salts with e.g. hydrochloric, hydrobromic, sulfuric, phosphoric, lactic, citric, tartaric, succinic, maleic or fumaric acid. Alkyl sulfonic acids (e.g. $CH_3SO_3H$) are also suitable for the salt formation. These salts may be in hydrated form.

Particularly preferred compounds of general Formula 1 are, however, the compounds of general Formula 1, wherein $R_1$ represents a hydrogen atom, an alkyl or F-alkyl group having 1 to 3 carbon atoms or an allyl group, $R_2$ represents a hydrogen atom, an alkyl group with 1 to 6 carbon atoms, a haloalkyl group having 1–6 carbon atoms, an allyl, propargyl, phenylethyl, 2-thienylethyl, 3-thienylethyl, cyclopropylmethyl group, and the acid addition salts thereof, particularly the physiologically acceptable acid addition salts.

According to the invention, the new compounds are obtained by the methods described in Schemes 1–4 (below).

The compounds of general Formula 1 which have at least one chiral centre can be resolved into their enantiomers by conventional methods, e.g. by column chromatography on a chiral phase, by fractional crystallization of the diastereomeric salts or by column chromatography of their conjugates, respectively, with optically active auxiliary acids such as tartaric acid, 0,0-dibenzoyltartaric acid, camphor acid, camphorsulfonic acid or α-methoxy-phenylacetic acid. Still another possibility is to form diastereomeric amines of Formula 1 (see Schemes 1 and 2) and to perform separation of these diastereomers by chromatography and/or fractional crystallization.

A pharmaceutical composition is provided by admixing the compound of Formula 1, or a therapeutically acceptable acid addition salt thereof, with a pharmaceutically acceptable carrier. The exact dosage and frequency of administration depends on the particular condition being treated, the severity of the condition being treated, the age, weight, general physical condition of the particular patient, other medication the individual may be taking, as is well known to those skilled in the art. Thus, the subject compounds, along with a pharmaceutically-acceptable carrier, diluent or buffer, can be administered in a therapeutic or pharmacological amount effective to alleviate the central nervous system disorder with respect to the physiological condition diagnosed. The compounds can be administered intravenously, intramuscularly, topically, transdermally such as by skin patches buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions. For oral administration, either solid or fluid unit dosage form can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms or oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

These compounds, and the physiologically acceptable acid addition salts thereof, have valuable pharmacological properties, particularly an effect on the central nervous system, particularly a stimulating effect on the dopamine receptors (either of, or both of, the autoreceptors and the postsynaptic receptors) or an inhibiting effect of the dopamine receptors, thus a partial agonist profile. The compounds of this invention possessing a high intrinsic efficacy for the dopamine receptors in the CNS of mammals are suitable for treating Parkinson's disease, either in mono-therapy or in combination therapy with e.g. L-DOPA and carbidopa. Such compounds are also anti-hyperprolacinergic drugs. The compounds of this invention possessing a low intrinsic efficacy (partial agonists, inverse agonists and/or antagonists) for the dopamine receptors in the CNS of mammals are suitable for treating psychotic disorders, e.g. schizophrenia The examples which follow are intended to further illustrate the invention:

The following experimental details of synthesis of some of the compounds claimed (see also Schemes 1–4, enclosed at the end of the respective examples) do not represent any limitation, whatsoever, of the present invention.

EXAMPLE 1

Synthesis of the enantiomers of 7-Amino-2-(N,N-di-n-propylamino)-thiazolo[4,5-g]tetralin (11a)
(Scheme 1)

4-Phthalimidophenylacetic acid (2)

Aminophenylacetic acid (1) is dissolved in glacial acetic acid, and phthalic anhydride is added. The reaction mixture is refluxed for 30 min., after which it is cooled. If the product precipitates, it is filtered off, otherwise it is worked up by extraction, evaporation of the solvents and chromatography on $SiO_2$.

6-Phthalimido-2-tetralone (3)

Compound 2 is suspended in $CH_2Cl_2$ and $SOCl_2$ is added. The mixture is refluxed until all of the acid 2 is dissolved (3–4 h) and the solvents are then evaporated, leaving the raw product of the acid chloride, which is used in the next reaction step without further purification, by redissolving it in $CH_2Cl_2$ and adding it dropwise to $AlCl_3$ in $CH_2Cl_2$ at a temperature of ca −5° C. To this mixture is a rapid stream of ethylene bubbled and after 1–2 h. The reaction mixture is cooled in an ice bath and ice-water is slowly added. The product 3 is worked up extractively and purification is performed via chromatography and/or destination or crystallization.

6-Phthalimido-2-(N-methylbenzyl)-aminotetralin (4)

6-Phthalimido-2-tetralone (3) and (S)-(−)-methylbenzylamine are dissolved in 1,2-dichloroethane. Sodium triacetoxyborohydride and a catalytic amount of glacial acetic acid are added to the reaction mixture. The reaction mixture is stirred for 48 h, the solvents are evaporated under reduced pressure and water is added to the residuals. The aqueous layer is basified with 10% $NaHCO_3$ and extracted with ethyl acetate. The combined organic layers are washed with brine, dried over $MgSO_4$, and concentrated under reduced pressure to give 4 as an oil.

6-Phthalimido-2-(N-α-methylbenzyl-N-propionyl) aminotetralin (5)

6-Phthalimido-2-(N-α-methylbenzyl)-aminotetralin (4) is dissolved in methylene chloride, cooled to 0° C., and triethylamine is added. A solution of propionyl chloride in methylene chloride is added dropwise over a 30 min period. After the addition is completed, the reaction mixture is stirred for 30 min. The mixture is washed with water, then with brine and dried over $MgSO_4$. The diastereomers are separated with column chromatography on silica and/or with preparative HPLC on e.g. straight phase Chromasil (10 μm, EKA Chemicals, Bohus, Sweden).

6-Amino-2-(N-α-methylbenzyl-N-propionyl)aminotetralin (6)

6-Phthalimido-2-(N-α-methylbenzyl-N-propionyl) aminotetralin (5) is dissolved in absolute ethanol after which hydrazine hydrate is added. The reaction mixture is stirred for 0.5 h at room temperature, after which the volatiles are removed under reduced pressure. The residue is refluxed in chloroform for 0.5 h, cooled to room temperature and filtered in order to remove the solid phthalimidohydrazine. The product 6 is obtained by concentrating the filtrate under reduced pressure.

6-Amino-2-(N-α-methylbenzyl-N-n-propyl)aminotetralin (7)

LiAlH$_4$ is suspended in dry ether, and the suspension is cooled on ice. A solution of 6-Amino-2-(N-α-methylbenzyl-N-propionyl)aminotetralin (6) in dry ether is added dropwise at a temperature of 0–25° C. After the addition is completed, the mixture is stirred on ice for 1 h, then at room temperature for 1 h, and then heated to reflux for 2 h. After cooling to room temperature, the reaction is quenched by the cautious addition of water, 4N NaOH and water (in that order). The mixture is heated to reflux until all precipitates have turned white (10 min), cooled to room temperature, and filtered over Celite. The filtrate is dried over Na$_2$SO$_4$ and concentrated under reduced pressure.

7-Amino-2-((N-α-methylbenzyl-N-n-propyl)amino)-thiazolo[4,5-g]tetralin (8)

6-Amino-2-(N-α-methylbenzyl-N-n-propyl)aminotetralin (7) and potassium thiocyanate are dissolved in glacial acetic acid. A solution of bromine in glacial acetic acid is added dropwise over a period of 15 min. After the addition is completed, the reaction mixture is stirred for 1.5 h, then basified with 10% NaOH and extracted with ethyl acetate. The combined organic layers are washed once with brine, dried over MgSO$_4$, and concentrated under reduced pressure. The product is purified with column chromatography over silica.

7-Amino-2-N-n-propylamino-thiazolo[4,5-g]tetralin (9)

7-Amino-2-(N-α-methylbenzyl-N-n-propyl)-thiazolo[4,5-g]tetralin (8) and ammonium formate are dissolved in methanol, and 10% Pd/C is added (under N$_2$). The reaction mixture is heated to reflux for 1 h. The Pd/C is removed by filtration over Celite, and the solvent is evaporated under reduced pressure. The residue is redissolved in acetonitril, the solids are removed by filtration and the product is obtained by evaporation of the solvents.

7-Amino-2-((N-propionyl-N-n-propyl)amino)-thiazolo[4,5-g]tetralin (10a)

7-Amino-2-N-n-propyl-thiazolo[4,5-g]tetralin (9) is converted to 10a as described for the conversion of 4 into 5.

7-Amino-2-(N,N-di-n-propylamino)-thiazolo[4,5-g]tetralin (11a)

7-Amino-2-(N-propionyl-N-n-propyl)-thiazolo[4,5-g]tetralin (10 a) is dissolved in dry ether, and BH$_3$ (solution in THF) is added dropwise, over a 1 h period. After the addition is completed, the reaction mixture is heated to reflux for 1 h. The mixture is cooled to room temperature, and water is added cautiously. Subsequently, 10% HCl is added, and all volatile solvents are evaporated under reduced pressure. The remaining aqueous solution is basified with 10% NaOH and extracted with ethyl acetate. The combined organic layers are dried over Na$_2$SO$_4$, and concentrated under reduced pressure.

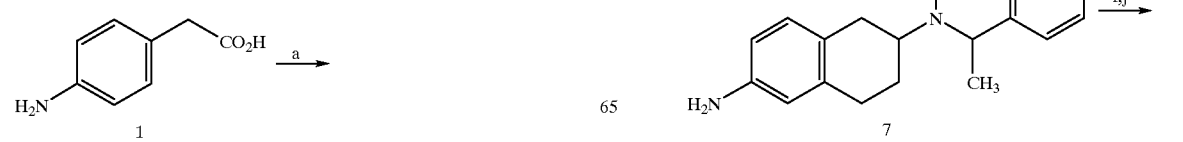

-continued

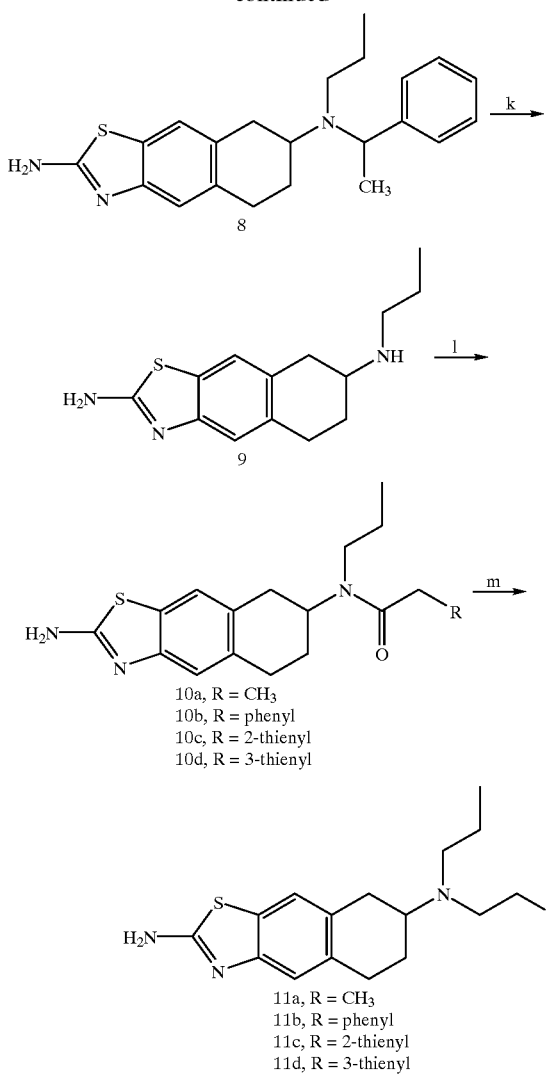

* Synthesis is performed analogous to Hansson et al, Synthesis and Pharmacology od Dipropyl(6,7,8,9-tetrahydro-3H-benzo[e]indol-7-yl)-amine enantiomers, 9[th] Noordwijkerhout-Camerino Symposium, May 23–27, 1993, Noordwijkerhout, The Netherlands (poster presentation). Reagents: (a) Phthalic anhydride, HOAc, Δ; (b) SOCl$_2$, CH$_2$Cl$_2$ Δ; (c) ethene, AlCl$_3$, benzene, 0° C.; (d) α-methyl-benzylamine, NaB(OAc)$_3$H, cat. HOAc, 1,2-dichloroethane; (e) propionyl-chloride, Et$_3$N, CH$_2$Cl$_2$; (f) separation of diastereomers; (g) H$_2$NNH$_2$.H$_2$O, EtOH, Δ; (h) LiAlH$_4$, Et$_2$O, r.t.; (i) KSCN, Br$_2$, HOAc, r.t.; (j) separation of possible regioisomers; (k) HCO$_2$NH$_4$, Pd/C 10%, MeOH, Δ; (l) acyl chloride, Et$_3$N, CH$_2$Cl$_2$; (m) BH$_3$ in THF, Et$_2$O, Δ.

EXAMPLE 2

Synthesis of 2-amino-thiazol-fused 2-aminotetralins in a separable mixture of regio isomers N,N-Di-n-propylamino tetralinxHCl (DPATxHCl; Mw 267.5; 5 mmol; 1.34 g) was dissolved in CH$_2$Cl$_2$ and 10% NaHCO$_3$ was added and extraction of the base to the organic layer was performed. The organic phase was separated, dried (Na$_2$SO$_4$) and filtered and the solvent was evaporated at reduced pressure, yielding an oil which was dissolved in TFA (10 mL) and at 0° C. KNO3 (5.5 mmol; 556 mg) was added in portions over ca 5 min. The reaction took place without any by-product formation, thus just the mono-NO$_2$ isomers were formed according to GC (100–10° C./min-280). The solvent TFA was evaporated under reduced pressure and the oily residue was dissolved in CH$_2$Cl$_2$ and water was added plus NaOH pellets, until pH was basic. Extraction, drying and evaporation yielded 1.0 g of an oil. GC/MS (100–10° C./min-320) shows four isomers: Rt=11.39 min.: M+ at m/e=276 (small) and the base peak at m/e=247 (M-29). Other products had the same MS but the GC retention times Rt=12.04, 12.53 and 12.59 min, respectively. The two last eluting peaks are predominant.

The raw oil containing the four nitro isomers was dissolved in MeOH (ca 50 mL) and NH$_4$HCOO (2 equiv.>>>2× 5×66.06=660 mg; take 1.0 g) was added together with Pd/C (10%); ca 100 mg). This mixture stirred over night in RT. No reduction took place in RT over night, but after ca 3 h of reflux the nitro isomers had been converted to amine isomers. GC/MS (100–10° C./min-320) shows four isomers: Rt=10.26 min: M+ at m/e=246 (small) and the base peak at m/e=146 (M-100). Another prominent peak was seen at m/e=217 (M-29). Other products had the same MS but the GC retention times Rt=10.42 and 11.02 min, respectively.

Acetylation (Ac$_2$O and Pyridine) gave the following GC/MS retention times: Rt=13.16, 14.00 and 14.38, respectively. GC/MS (100–10° C./min-320) shows three (or maybe four if there is overlap in one of the peaks) isomers all with similar spectra: M+ at m/e=288 (small) and the base peak at m/e=259 (M-29). Other prominent peaks were seen at m/e= 146 and 188.

A mixture (660 mg; Mw=246 .>>>2.68 mmol) of two or more of the NH2-DPAT isomers (one major peak on GC (100–10° C./min-280) at Rt=12.48 min; 2–4 major that had been acetylated: Rt=14.98 min (14%), Rt=15.86 min (30%) and Rt=16.57 min (51%)) was dissolved in HOAc (10 mL) and KSCN (Mw=97.18; 2×2.68×97.18=521 mg) was added. To this mixture was added also Br$_2$ (1×2.68×160/3.11=138 μL in 2 mL HOAc over 15 min in RT.

The reaction went well and after 2 h water and NaOH(s) were added to alkaline reaction and the mixture was extracted with EtOAc and later with CH$_2$Cl$_2$. The organic layers were pooled, dried and filtered and the solvents were evaporated under reduced pressure leaving an oil (ca 0.97 g).

GC/MS (100–10° C./min-320) shows four (or maybe more (maximally 6) if there is overlap in one or more of the peaks) isomers, all but one with similar spectra: Rt=15.45 has M+ at m/e=303 (small) and the base peak at m/e=72. Other prominent peaks were seen at m/e=274 (M-29) and 176 (M-100).This spectrum is somewhat different to the other peaks in the chromatogram: Rt=16.27 shows has M+ at m/e=303 (small) and the base peak at m/e=203 (M-100). Another prominent peak is m/e=274 (M-29). Other peaks in the GC/MS chromatogram having this mass spectrum are found at Rt=16.40 and Rt=16.50 min.

The raw product (oil) was chromatographed on SiO$_2$ (ca 100 g and eluting with CH$_2$Cl$_2$, CH$_2$Cl$_2$:MeOH in the compositions sequentially, 20:1, 10:1 and 5:1). Fractions were about 10 mL of volume and the solvents were flashed through the column.

Fr 14–18 were pooled and evaporated: 19 mg; no NMR; GC/MS shows no interesting peaks but the starting material DPAT.

Fr 19–24 were pooled and evaporated: 17 mg; no NMR; GC/MS shows no interesting peaks but the starting material DPAT.

Fr 25–28 were pooled and evaporated: 20 mg; NMR shows one singlet at δ=7.0 ppm. The other singlet (δ=7.2 ppm) is CHCl₃. This makes sense because the GC/MS spectrum of these collected fractions show a big peak for the brominated product (m/e=388).

Fr 37–46 were pooled and evaporated: 80 mg; NMR shows what initially could be interpreted as an AB spectrum, but the doublets do not lean in the right direction (roof effect), something which is seen with the other fractions below. Thus a two dimensional experiment was initiated (500 MHz machine). This experiment indicates that here is coupling between the protons (thus doublets at δ=7.2 and 7.0; J=8 Hz). However, the spectrum also contains two singlets (10–20% of the intensity of the putative doublets) at δ=7.28 and 7.24. This may indicate that the mixture of compounds in the pooled fractions 37–46 could contain one of the two claimed products shown here:

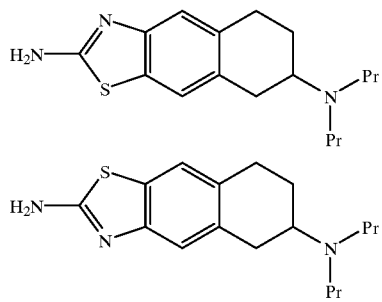

By close inspection of the GC/MS peak (Rt=16.36 min) from this fraction (37–46), it was seen that the peak was split. A TLC did also show (TLC on SiO₂ eluting with CH₂Cl₂:MeOH 5:1 and applying a concentrated solution) two spots. The results from these two techniques may argue for a mixture of the two "straight rings" isomers depicted above.

Fr 43 was singled out (9 mg) and was separately run on GC/MS and NMR (300 MHz). GC/MS shows at Rt=16.43 min M+ at m/e=303 and the base peak at m/e=203. Another prominent peak was at m/e=294 (M-29). This GC/MS peak was not split and thus Fr 43 may contain one of the two "straight rings" isomers depicted above.

Fr 37–46 (10 mg) was taken out and was dissolved in 23 mg HOAc and diluted with water to a total volume of 1.2 mL. One rat was injected s.c. in the neck region with the dose 10 mg/kg and displayed the 5-HT behavioral syndrome after ca 5 min. Lower lip retraction was also very prominent and lasted for ca 4 h. Thus, the mixture of isomers in Fr 37–46 contains one or several pharmacologically active compounds, possibly one or both of the "straight rings" isomers depicted above.

Fr 47–55 were pooled and evaporated: 141 mg; GC/MS shows a major peak at Rt=16.30 min, showing M+ at m/e=303 and the base peak at m/e=203. Another prominent peak was m/e=274 (M-29). NMR shows an obvious coupling in an AB spectrum (o-protons; δ=7.06 (d, J=8 Hz) and δ=6.86 (d, J=8 Hz).

Fr 62–66 were pooled and evaporated: 51 mg; No GC/MS was run; NMR shows an obvious coupling in an AB spectrum (o-protons; δ=7.06 (d, J=8 Hz) and 6.92 (d, J=8 Hz).

Comments: In order to make the "multi target synthesis" described above more efficient, one should employ semi-preparative and/or preparative HPLC on one or several of the product (isomeric) mixtures NO2-DPAT, NH2-DPAT or 2-aminothiazol-DPAT. This can be done in the straight phase or in the reversed phase modes.

An alternative route to these "straight rings" isomers depicted above is to start from the known 6-amino-2-(N,N-dipropylamino)teralin (CAS RN 83343-17-3) and known 7-amino-2-(N,N-dipropylamino)teralin (CAS RNs 200350-40-9, 129462-30-2, 129462-29-9 and 83343-37-7for the R-enantiomer, the (−)-enantiomer, the (+)-enantiomer and the racemic mixture, respectively) and apply the reaction with KSCN and Br2 in HOAc, as described above and also at other places in this experimental section (e.g. see the synthesis of compound 22 below).

EXAMPLE 3

Synthesis of the enantiomers of 6-Amino-2-(N,N-di-n-proalamino)-thiazolo[4,5-f]indan (22) (Scheme 2)

5-Nitro-2-(N--methylbenzyl)-aminoindene (13)
5-Nitro-indan-2-one (CAS RN [116530-60-0]; 12), (S)-(−)-α-methylbenzylamine and a catalytic amount of para-toluenesulfonic acid are dissolved in toluene and refluxed under a nitrogen atmosphere under Dean-Stark conditions. After 5 h the product is obtained by removing the volatiles under reduced pressure.

5-Amino-2-(N-α-methylbenzyl)-aminoindan (14)
5-Nitro-2-(N-α-methylbenzyl)-aminoindene (13) is dissolved in methanol, and 10% Pd/C is added (under N₂). The reaction mixture is placed in a Parr apparatus, and is shaken for <1 h with a hydrogen gas pressure of 1.0 atm. The Pd/C is removed by filtration over Celite, and the product is obtained by evaporating the solvent under reduced pressure.

5-Phthalimido2-(N-α-methylbenzyl)-aminoindan (15)
5-Amino-2-(N-α-methylbenzyl)-aminoindan (14) is dissolved in glacial acetic acid, and phthalic anhydride is added. The reaction mixture is refluxed for 30 min., after which it is cooled. The product precipitates and is filtered off.

5-Phthalimido-2-(N-α-methylbenzyl-N-propionyl-)-aminoindan (16)
5-Phthalimido-2-(N-α-methylbenzyl)-aminoindan (15) is dissolved in methylene chloride, cooled to 0° C., and triethylamine is added. A solution of propionyl chloride in methylene chloride is added dropwise over a 30 min period. After the addition is completed, the reaction mixture is stirred for 30 min. The mixture is washed with water, then with brine and dried over MgSO₄. The diastereomers are separated with column chromatography on silica and/or with preparative HPLC on e.g. straight phase Chromasil (10 μm, EKA Chemicals, Bohus, Sweden).

5-Amino-2-(N-α-methylbenzyl-N-propionyl)-aminoindan (17)
5-Phthalimido2-(N-α-methylbenzyl-N-propionyl-)-aminoindan (16) is dissolved in absolute ethanol after which hydrazine hydrate is added. The reaction mixture is stirred for 0.5 h at room temperature, after which the volatiles are removed under reduced pressure. The residue is refluxed in chloroform for 0.5 h, cooled to room temperature and filtered in order to remove the solid phthalimidohydrazine. The product is obtained by concentrating the filtrate under reduced pressure.

6-Amino-2-((N-α-methylbenzyl-N-propionyl)amino)-thiazolo[4,5-f]indan (18)
5-Amino-2-(N-methylbenzyl-N-propionyl)-aminoindan (17) and potassium thiocyanate are dissolved in glacial acetic acid. A solution of bromine in glacial acetic acid is added dropwise over a period of 15 min. After the addition is completed, the reaction mixture is stirred for 1.5 h, then basified with 10% NaOH and extracted with ethyl acetate. The combined organic layers are washed once with brine, dried over MgSO$_4$, and concentrated under reduced pressure. If not separated at the stage of compound 16, the diastereomers are separated with column chromatography on silica and/or with preparative HPLC on e.g. straight phase Chromasil (10 μm, EKA Chemicals, Bohus, Sweden).
6-Amino-2-((N-α-methylbenzyl-N-n-propyl)amino)-thiazolo[4,5-f]indan (19)

LiAlH$_4$ is suspended in dry ether, and the suspension is cooled on ice. A solution of 6-Amino-2-(N-α-methylbenzyl-N-propionyl)-thiazolo[4,5-f]indan (18) in dry ether is added dropwise. After the addition is completed, the mixture is stirred on ice for 1 h, then at room temperature for 1 h, and then heated to reflux for 2 h. After cooling to room temperature, the reaction is quenched by the cautious addition of water, 4N NaOH and water (in that order). The mixture is heated to reflux until all precipitates have turned white (10 min), cooled to room temperature, and filtered over Celite. The filtrate is dried over Na$_2$SO$_4$ and concentrated under reduced pressure.
6-Amino-2-(N-n-propylamino)-thiazolo[4,5-f]indan (20)

6-Amino-2-((N-α-methylbenzyl-N-n-propyl)amino)-thiazolo[4,5-f]indan (19) and ammonium formate are dissolved in methanol, and 10% Pd/C is added (under N$_2$). The reaction mixture is heated to 50° C. for 1 h. The Pd/C is removed by filtration over Celite, and the solvent is evaporated under reduced pressure. The residue is redissolved in acetonitril, the solids are removed by filtration and the product is obtained by evaporation of the solvents.
6-Amino-2-((N-propionyl-N-n-propyl)amino)-thiazolo[4,5-f]indan (21)

6-Amino-2-(N-n-propylamino)-thiazolo[4,5-f]indan (20) is converted to 21 as described for the conversion of 15 into 16.
6-Amino2-(N,N-di-n-propylamino)-thiazolo[4,5-f]indan (22)

6-Amino-2-(N-propionyl-N-n-propyl)amino)-thiazolo[4,5-f]indan (21) is dissolved in dry ether, and BH3$_3$ (solution in THF) is added dropwise, over a 1 h period. After the addition is completed, the reaction mixture is heated to reflux for 1 h. The mixture is cooled to room temperature, and water is added cautiously. Subsequently, 10% HCl is added, and all volatile solvents are evaporated under reduced pressure. The remaining aqueous solution is basified with 10% NaOH and extracted with ethyl acetate. The combined organic layers are dried over Na$_2$SO$_4$ and concentrated under reduced pressure.

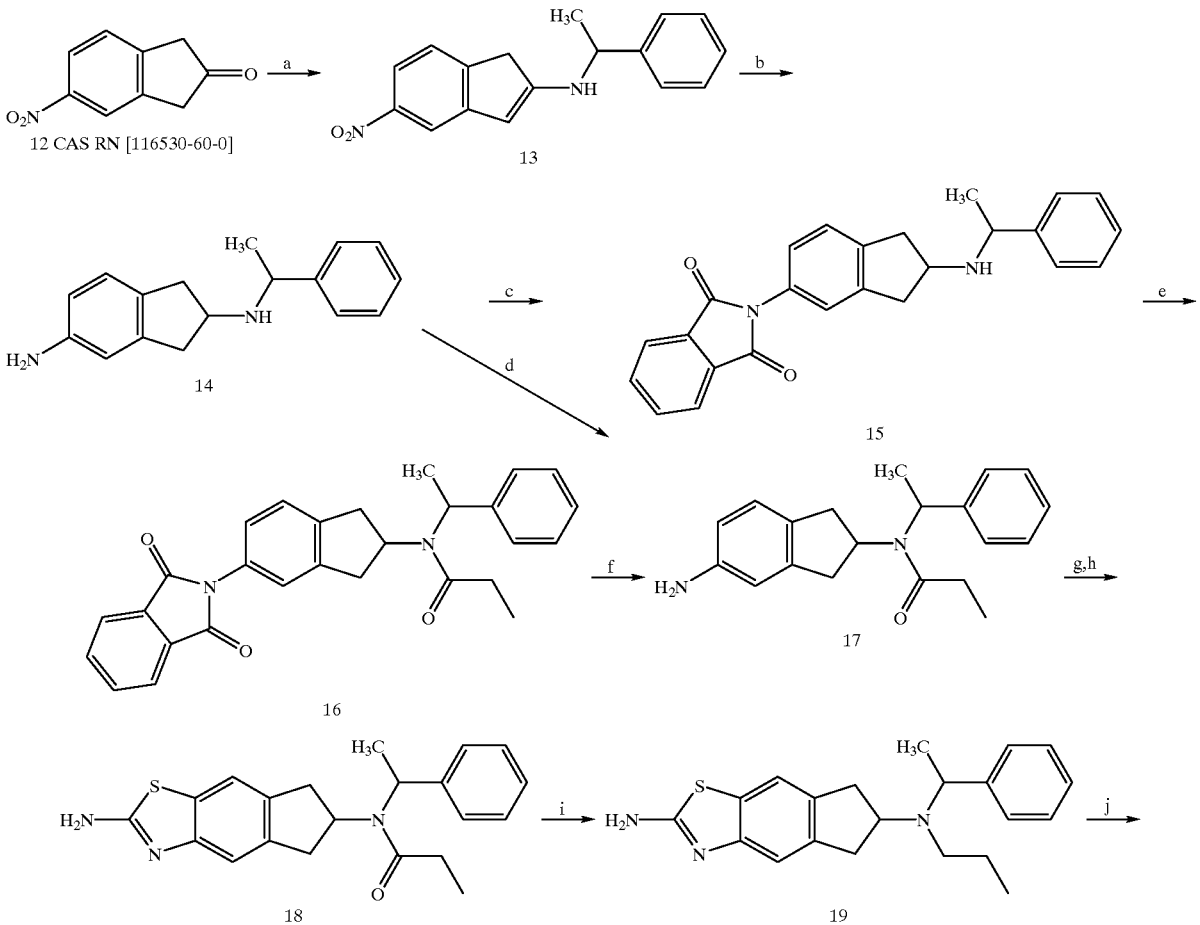

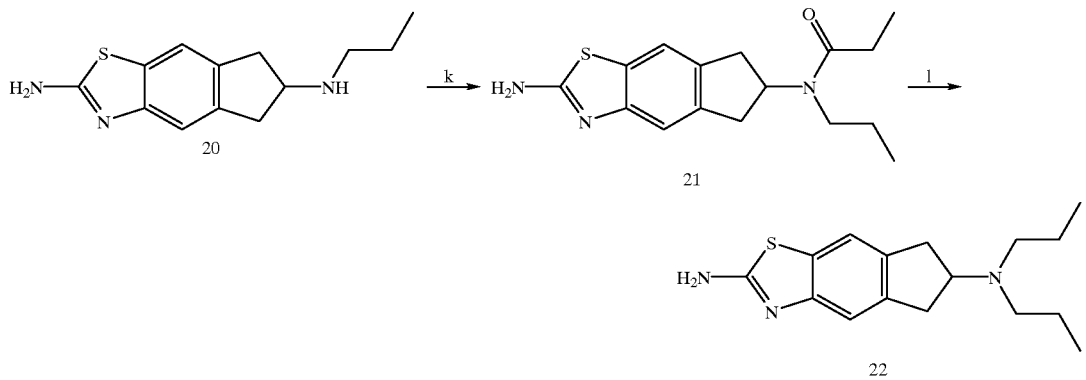

-continued

Reagents: (a) α-methyl-benzylamine, cat. p-TosOH, toluene, Δ; (b) H$_2$, Pd/C 10%, MeOH; (c) Phtalic anhydride, HOAc, Δ; (d) propionylchloride, Et$_3$N, CH$_2$Cl$_2$; (e) propionylchloride, Et$_3$N, CH$_2$Cl$_2$; (f) H$_2$NNH$_2$.H$_2$O, EtOH, Δ; (g) KSCN, Br$_2$, HOAc, r.t.; (h) separation of diastereomers and possible regioisomers; (i) LiAlH$_4$, Et$_2$O, r.t.; (j) HCO$_2$NH$_4$, Pd/C 10%, MeOH, Δ; (k) propionylchloride, Et$_3$N, CH$_2$Cl$_2$; (l) BH$_3$ in THF, Et$_2$O, Δ.

EXAMPLE 4

Synthesis of racemic 6-Amino-2-N-n-propylamino-thiazolo[4,5-f]indan (20) (Scheme 3)

2-Propionamidoindan (24)

2-Aminoindan hydrochloride 23 (2.0 g, 11.8 mmol) and sodium hydrogencarbonate (2.8 g, 32.8 mmol) were dissolved in a well-stirred two-layer system of 36 mL of water and 80 mL of ethyl acetate. The mixture was cooled to 0° C. and a solution of propionyl chloride (1.1 mL, 12 mmol) in 25 mL of ethyl acetate was added dropwise over a 30 min period. After the addition was completed, the mixture was stirred for an additional 30 min. The two layers were separated and the water layer was extracted twice with ethyl acetate. The combined organic layers were washed with brine, dried over MgSO$_4$, and concentrated under reduced pressure, which yielded 21 as a white crystalline solid (1.52 g, 67%): mp 116–118° C.; $^1$H-NMR (CDCl3, 200MHz) 1.13 (t, J=7.6, 3H), 2.15 (q, J=7.6, 2H), 2.78 (dd, J1=16.2, J2=4.3, 2H), 3.31 (dd, J1=16.2, J2=7.0, 2H), 4.71–4.80 (m, 1H), 5.87 (br s, 1H), 7.15–7.32 (m, 4H); $^{13}$C NMR 9.5, 29.5, 40.0 (2C), 50.2, 124.7 (2C), 126.6 (2C), 140.8 (2C), 173.6; MS (EIPI) m/e 189 (M+). C$_{12}$H$_{15}$NO.$^0$H$_2$O: C: 74.42 (74.70), H: 8.01 (7.85), N: 7.24 (7.28).

5-Amino-2-propionamidoindan (25)

Amide 24 (1.0 g, 5.5 mmol) was dissolved in nitromethane (18 mL), and cooled on ice. A nitrating mixture consisting of 0.74 mL conc. nitric acid, 1.6 ml of water and 10 mL of conc. sulfuric acid was added dropwise over a 30 min period. After the addition was completed, the reaction mixture was stirred for 1 h, while gradually warming to room temperature. The reaction was quenched with ice, and the reaction mixture was extracted with ethyl acetate. The combined organic layers were washed once with brine, dried over MgSO$_4$, and concentrated under reduced pressure, yielding a yellow solid (1.2 g, 95%), which consisted mainly (82% according to GC) of 5-nitro-2-propionamidoindan.

The nitro-compound (1.2 g, containing 4.3 mmol of 5-nitro-2-propionamidoindan) and ammonium formate (1.4 g, 22.2 mmol) were dissolved in 55 mL of methanol. This mixture was treated (under N$_2$) with 10% Pd/C (0.56 g), and subsequently stirred at 50° C. for 45 min. After cooling to room temperature, the Pd/C was removed by filtration over Celite, and the methanol was evaporated under reduced pressure. The remaining pink solid was purified with MPLC on silica (initial eluent 100% hexane, final eluent 100% ethyl acetate), giving 22 as a white solid (0.67 g, 76%): mp 127–128° C.; $^1$H-NMR (CDCl$_3$, 200 MHz) 1.08 (t, J=7.7, 3H), 2.10 (q, J=7.6, 2H), 2.62 (dt, J1=16.1, J2=4.2, 2H), 3.14 (dd, J1=16.2, J2=7.1, 2H), 3.61 (s, 2H), 4.59–4.67 (m, 1), 6.12 (d, J=7.3, 1H), 6.45–6.51 (m, 2H), 6.94 (d, J=7.8, 1H); $^{13}$C NMR 9.6, 29.4, 38.9,40.0, 50.5 111.5, 113.7, 125.1, 130.5, 142.2, 145.4, 173.6; MS (EIPI) m/e 204 (M+). Anal Calcd (Obsd) for C$_{12}$H$_{16}$N$_2$: C: 70.59 (70.37), H: 7.84 (7.82), N: 13.73 (13.67).

5-Amino-2-N-n-propylaminoindan (26)

Amide 25 (0.62 g, 3.0 mmol) was dissolved in 8 mL of dry ether, and BH$_3$ (16 mL of a 1 M solution in THF) was added dropwise, over a 1 h period. After the addition was completed, the reaction mixture was heated to reflux for 1 h. The mixture was cooled to room temperature, and 1.6 mL of water was added cautiously. Subsequently, 3.2 mL of 10% HCl was added, and all volatile solvents were evaporated under reduced pressure. The remaining aqueous solution was basified with 10% NaOH and extracted with ethyl acetate (2 20 mL). The combined organic layers were dried over Na$_2$SO$_4$ and concentrated under reduced pressure, which yielded 23 as a clear oil (0.52 g, 90%): $^1$H-NMR (CDCl$_3$, 200 MHz) 0.92 (t, J=7.3, 3H), 1.43–1.61 (m, 2H), 2.58–2.71 (m, 4H), 3.00–3.11 (m, 2H), 3.52–3.65 (m, 3H), 6.49 (d, J=7.8, 1H), 6.55 (s, 1H), 6.96 (d, J=7.8, 1H); $^{13}$C NMR 11.6, 23.2, 38.9, 39.9, 50.0, 59.8, 111.5, 113.4, 125.0, 131.6, 142.9, 145.0; MS (EIPI) m/e 190 (M+). Part of the product was converted to the dihydrochloride and recrystallized from ethanol, yielding white crystals: mp 238–242° C. Anal Calcd (Obsd) for C$_{12}$H$_{18}$N$_2$.2HCl: C: 54.96 (54.59), H: 7.63 (7.66), N: 10.69 (10.46).

6-Amino-2-N-n-propylamino-thiazolo[4,5-f]indan (20)

Compound 26 (0.48 g, 2.5 mmol) was converted to 20 (0.29 g, 46%), as described for the conversion of 17 into 18. The product was converted to the dihydrochloride and recrystallized from methanol/ethanol, which yielded a white solid: mp 285–290° C.; $^1$H-NMR (D$_2$O, 200 MHz) 0.81 (t, J=7.3, 3H), 1.48–1.60 (m, 2H), 2.92 (t, J=7.7, 2H), 2.96–3.08 (m, 2H), 3.26–3.38 (m, 2H), 3.95–4.08 (m, 1H), 7.15 (s, 1H), 7.40 (s, 1H); $^{13}$C NMR 9.9, 19.1, 34.9, 35.2, 47.5, 57.9, 109.7, 118.3, 121.9, 136.1, 136.2, 139.5, 169.2; IR (KBr, cm-1) 2967, 2805, 2658, 1651, 1459; MS (EIPI)

m/e 247 (M+). Anal Calcd (Obsd) for C$_{13}$H$_{17}$N$_3$S1.2HCl.?H$_2$O: C: 47.37 (47.78), H: 6.07 (6.07), N: 12.75 (12.88).

Scheme 3

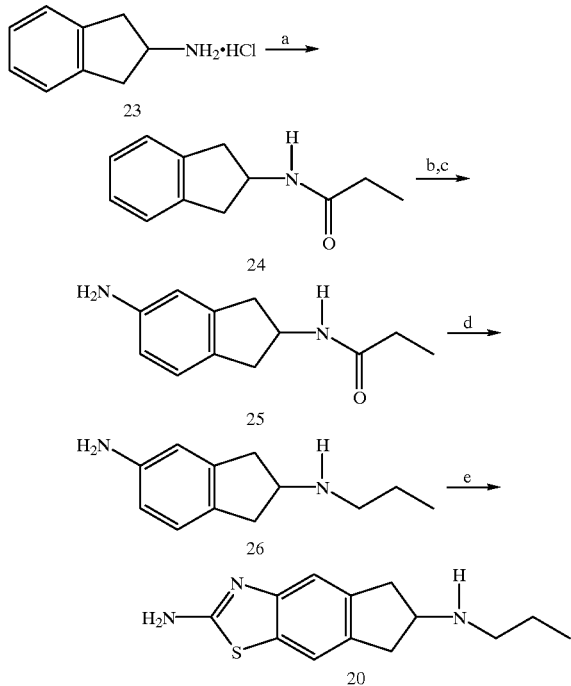

Reagents: (a) propionyl chloride, NaHCO$_3$, H$_2$O, EtOAc; (b) HNO$_3$/H$_2$SO$_4$/H$_2$O, MeNO$_2$ 0° C.; (c) NH$_4$CO$_2$, 10% Pd/C, MeOH, 50° C.; (d) BH$_3$ in THF, Et$_2$O, r.t.→reflux; (e) KSCN, Br$_2$, AcOH.

EXAMPLE 5

Synthesis of racemic 6-Amino-2-(N,N-di-n-propylamino)-thiazolo[4,5-f]indan (22) and 5-Amino-2-(N,N-di-n-propylamino)-thiazolo[5,4-e]indan (31; this compound falls outside the compounds of this invention) (Scheme 4)

2-N-n-Propylaminoindan (27)

2-Propionamidoindan (24, 0.83 g, 4.4 mmol) was converted to 28 (0.75 g, 98%), as described for the reduction of 25. A small amount was converted to the hydrochloride and recrystallized from 2-propanol, which yielded white crystals: mp 191–192° C.; $^1$H-NMR (CDCl$_3$, 200 MHz) 1.04 (t, J=7.3, 3H), 1.70–1.82 (m, 2H), 3.01–3.20 (m, 4H), 3.29–3.48 (m, 2H), 4.00–4.11 (m, 1H), 7.18–7.30 (m, 4H); $^{13}$C NMR 9.7, 19.3, 35.5 (2C), 47.6, 58.0, 124.2 (2C), 127.0 (2C), 138.6 (2C). HRMS calcd. (obsd.) for C$_{12}$H$_{17}$N 175.1361 (175.1364).

2-(N-n-Propyl-N-propionyl)aminoindan (28)

Compound 27 (0.75 g, 4.3 mmol) was converted to 28 as described for the conversion of 23 to 24. The product was purified with MPLC on silica (initial eluent 100% hexane, final eluent hexane: ethyl acetate=1:1), yielding 28 as a clear oil (0.73 g, 74%). $^1$H-NMR (CDCl$_3$, 200 MHz) 0.83 (t, J=7.3, 3H), 1.16 (t, J=7.3, 3H), 1.49–1.63 (m, 2H), 2.35–2.46 (m, 2H), 3.03–3,.22 (m, 6H), 4.65–4.83 (m, ?H), 5.08–5.25 (m, ?H), 7.16–7.19 (m, 4H). HRMS calcd. (obsd.) for C$_{15}$H$_{21}$NO 231.1623 (231.1614).

5-Amino-2-(N-n-propyl-N-propionyl)aminoindan (29)

Compound 28 (0.70 g, 3.0 mmol) was converted to 5-nitro-2-(N-n-propyl-N-propionyl)aminoindan, which subsequently was reduced to 29 as described for the conversion of 24 into 25. The product was purified with MPLC on silica (initial eluent 100% hexane, final eluent hexane:ethyl acetate=1:1), yielding 29 as a light-yellow oil (0.49 g, 66%). $^1$H-NMR (CDCl$_3$, 200 MHz) 0.83 (t, J=7.3, 3H), 1.15 (t, J=7.3, 3H), 1.48–1.65 (m, 2H), 2.32–2.43 (m, 2H), 2.93–3.01 (m, 4H), 3.05–3.21 (m, 2H), 3.61 (br s, 2H), 4.60–4.77 (m, ?H), 5.10–5.28 (m, ?H), 6.50 (d,J=7.6, 1H), 6.54 (s, 1H), 6.96 (d, J=7.6, 1H); $^{13}$C NMR (CD$_3$OD, 200 MHz) 8.6, 10.0, 22.4, 26.3, 35.9, 36.0, 43.9, 57.1, 111.4, 114.3, 124.2, 130.4, 141.5, 145.4, 175.0. HRMS calcd. (obsd.) for C$_{15}$H$_{22}$N$_2$O 246.1732 (246.1720).

5-Amino-2-(N-di-n-propylamino)indan (30)

Compound 29 (0.43 g, 1.8 mmol) was converted to 30 (0.39 g, 96%) as described for the reduction of 25 to 26. $^1$H-NMR (CDCl$_3$, 200 MHz) 0.88 (t, J=7.3, 6H), 1.42–1.57 (m, 4H), 2.47–2.55 (m, 4H), 2.77–3.00 (m, 4H), 3.55–3.67 (m, 1H), 6.49 (d, J=7.8, 1H), 6.54 (s,1H), 6.95 (d, J=7.8, 1H); $^{13}$C NMR 11.7 (2C), 19.7 (2C), 35.4, 36.5, 53.2 (2C), 63.3, 111.3, 113.4, 124.8, 131.8, 142.9, 144.9. HRMS calcd. (obsd.) for C$_{15}$H$_{24}$N$_2$ 232.1939 (232.1936).

6-Amino-2-(N,N-di-n-propylamino)-thiazolo[4,5f]indan (22) and 5Amino-2-(N,N-di-n-propylamino)-thiazolo[4,5e]indan (31)

Compound 30 (0.35 g, 1.5 mmol) was converted to a mixture of 22 and 31, as described for the conversion of 7 into 8. The products were separated with MPLC on silica (initial eluent hexane:ethyl acetate=1:1, final eluent ethyl acetate:ethanol=1:1), which yielded 22 as a light yellow solid (0.18 g, 41%), and 31 as a light yellow solid (0.11 g, 25%).

22: $^1$H-NMR (CD$_3$OD, 200 MHz) 0.94 (t, J=7.3, 6H), 1.57–1.66 (m, 4H), 2.70–2.78 (m, 4H), 2.92–3.25 (m, 4H), 3.65–3.88 (m, 1H), 7.20 (s, 1H), 7.37 (s, 1H); $^{13}$C NMR 10.3 (2C), 17.8 (2C), 35.1, 35.4, 52.5 (2C), 63.3, 113.1, 116.0, 129.1, 134.0, 138.4, 150.8, 168.2; IR (KBr, cm-1) 2967, 2632, 1638; MS (EIPI) m/e 289 (M+). The compound was converted to the dihydrochloride and recrystallized from 100% ethanol, which yielded an off-white solid, mp: 273–275° C. (dec). Anal Calcd (Obsd) for C$_{16}$H$_{23}$N$_3$S.2HCl.1/2H$_2$O: C: 51.89 (52.02), H: 6.49 (6.82), N: 11.35 (11.28). 31: $^1$H-NMR (CD$_3$OD, 200 MHz) 0.89 (t, J=7.3, 6H), 1.46–1.57 (m, 4H), 2.49–2.57 (m, 4H), 2.72–3.18 (m, 4H), 3.52–3.78 (m, 1H), 7.06 (d, J=8.1, 1H), 7.18 (d, J=8.1, 1H); $^{13}$C NMR 10.6 (2C), 18.7 (2C), 35.6, 35.8, 52.6 (2C), 62.9, 115.7, 121.4, 126.0, 133.4, 134.7, 150.8, 167.5; IR (KBr, cm-1) 2966, 2717, 2633, 1637, 1458; MS (EIPI) m/e 289 (M+). The compound was converted to the dihydrochloride and recrystallized from 100% ethanol, which yielded an off-white solid, mp: 233–237° C. (dec.). HRMS calcd. (obsd.) for C$_{16}$H$_{23}$N$_3$S 289.1613 (289.1619).

Scheme 4

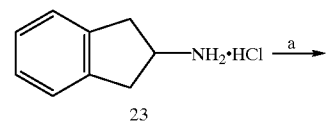

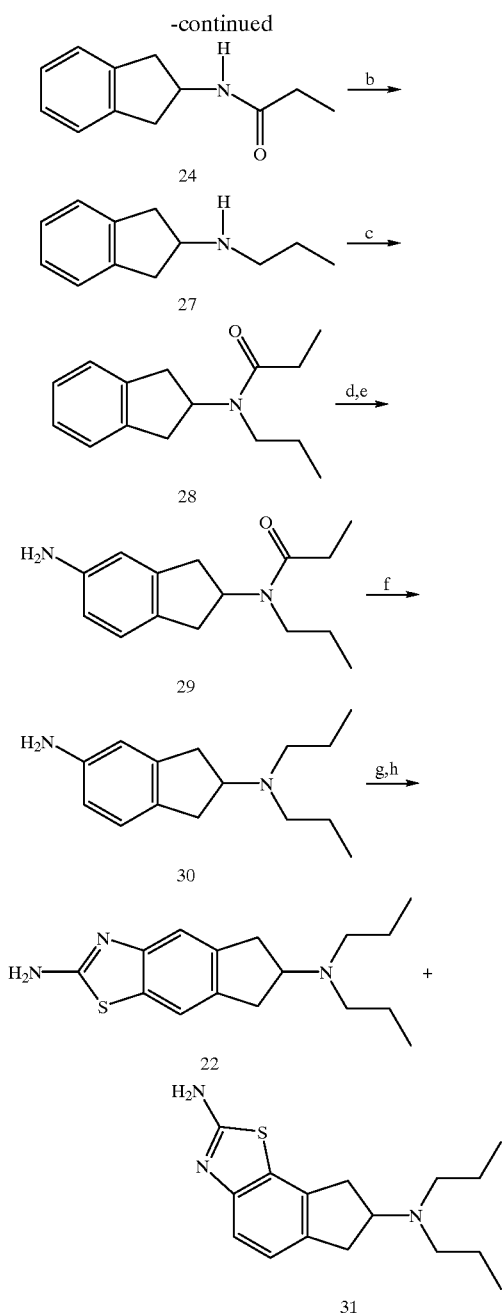

Reagents: (a) propionyl chloride, NaHCO₃, H₂O, EtOAc; (b) BH₃ in THF, Et₂O, r.t.→reflux; (c) propionyl chloride, Et₃N, CH₂Cl₂; (d) HNO₃/H₂SO₄/H₂O, MeNO₂, 0° C.; (e) NH₄CO₂, 10% Pd/C, MeOH, 50° C.; (f) BH₃ in THF, Et₂O, r.t.→reflux; (g) KSCN, Br₂, AcOH; (h) separation of isomers with column chromatography on SiO₂.

Pharmacology

The compounds of this invention may be pharmacologically characterized by one of several of the following methods. The combination of such methods is valuable for the estimation of the affinities and intrinsic efficacies of the compounds of this invention. The methods given below serve as examples and are not intended to limit the pharmacological scope of the invention.

DA Receptor Binding

The compounds of this invention may be assayed in conventional in vitro binding test models using e.g. human dopamine (DA) D2L, D3 or D4.2 receptors, expressed in Chinese hamster ovary (CHO) K-1 cells. In the antagonist binding studies, the affinity of the compounds is determined by their ability to displace [3H]-spiperone from D2L, D3 or D4.2 DA receptors. In the agonist binding studies, the affinity for the D2L DA receptor is determined using [3H]-N-0437 (5-hydroxy-2-(N-n-propyl-N-(2-thienylethyl)amino)tetralin) or [3H]-NPA (N-propyl-norapomorphine), as the radioligand. The affinity data obtained with [3H]-NPA are comparable to those obtained with [3H]-N-0437.

Intrinsic Activity (in vitro methods)

The intrinsic efficacy of the compounds of the present invention can be determined with, at least, two different functional tests in vitro: i) the mitogenesis assay (Lajiness et al. JPET, 1993, 267, 1573–1581, Chio et al. Mol. Pharmacol. 1994, 45, 51–60). [3H]-Thymidine uptake is determined in CHO-L6 cells transfected with the human DA D2 or D3 receptor, ii) the c-AMP method (Pugsley et al. JPET, 1995, 274, 898–911).

Contralateral Turning in 6-OH-DA Lesioned Rats

The compounds of the present invention may be evaluated in rats unilaterally lesioned with 6-OH-DA (Ungerstedt and Arbuthnott, Brain Res. 1970, 24, 485493). In this model, the DA neurons of one side (left or right) of the nigrostriatal DA system are selectively and completely degenerated by intracebral injection of the neurotoxin 6-OH-DA. This causes a postsynaptic super-sensitivity to develop on the lesioned side. Upon systemic administration of a DA agonist, the rat will start to turn contralaterally, i.e. towards the non-lesioned side. The evoked turning behavior is a measure of the DA (D1 and/or D2) agonist properties of a compound.

Microdialysis in Rat Striatum

Male Wistar rats (from Harlan, Zeist, The Netherlands) weighing 280–320 g were used, and housed as described for the locomotor activity experiments. On line brain microdialysis in freely moving animals was essentially performed as described previously (Westerink, Trends in Anal. Chem. 1992, 11, 176–182). Briefly, rats were anesthetized with choral hydrate (400 mg/kg ip) and 10% lidocaine locally applied. The rats were then mounted into a stereotaxic frame (Kopf). The incisor bar was placed in position so that the scull was held in a horizontal position. The skull was exposed and burr holes were drilled. An Y-shaped cannula was used for the experiments, with an exposed tip length of 3 mm. The dialysis tube (ID: 0.22 mm; OD: 0.31 mm) was prepared from polyacrylonitrile methalys sulfonate copolymer (AN 69, Hospal, Bologna, Italy). The dialysis membrane was implanted in the Striatum with coordinates which were calculated relative to bregma: A+1, L 3, D 6 according to the brain atlas of Paxinos and Watson (1982). The dura was removed with a sharp needle. Two anchor screws were positioned in different bone plates nearby. Before insertion into the brain the dialysis probes were perfused with successively ultra pure water, methanol, ultra pure water and Ringer solution (1.2 mM Ca2+). The dialysis probe was positioned in the burr hole under stereotaxic guidance. The probe was cemented in this position with phosphatine dental cement (Associated dental products LTD, Kemdent Works, Purdon, Swinden, Wiltshire SN 5 9 HT).

The experiments were performed in conscious rats 17–56 h after implantation of the cannula. The striatum was perfused with a Ringer solution (147 mM NaCl, 4 mM KCl, 1.2 mM CaCl₂, 1.1 mM MgCl₂) at 2 l/min (CMA/102 microdialysis pump). After the experiments the rats were sacrificed and the brains were removed. After removal the brains were kept in 4% paraformaldehyde solution until they were sectioned to control the location of the dialysis probes.

Dopamine, DOPAC and 5-HIAA were quantitated by HPLC with electrochemical detection. An HPLC pump (LKB, Pharmacia) was used in conjugation with an EC-detector (Antec, Leiden) working at 625 mV versus Ag/AgCl reference electrode. The analytical column was a Supelco Supelcosil LC-18 Column (15 cm, 4.6 mm, 3 µm). The mobile phase consisted of a mixture of 4.1 g/l sodium acetate (Merck), 85 mg/l octane sulphonic acid (Aldrich), 50 mg/l EDTA (Merck), 8.5% methanol (Labscan) and ultra pure water (pH=4.1 with glacial acetic acid).

Statistics: The microdialysis data were analyzed using Friedman Repeated Measures Analysis of Variance on Ranks with as post-hoc test Dunnetts Method.

The effects of 22 on in vivo DA turnover in rat striatum were assessed with microdialysis methods.

Inhibition of D-Amphetamine-Induced Hypermotility in Rats

The hypermotility tests were carried out essentially as described by Arnt, J. (Eur. J. Pharmacol. 1995, 283, 55–62). Male Wistar rats (Harlan, Zeist, the Netherlands) weighing 200–250 g were used. Until the experiment, rats were group-housed with food and water available ad libitum, lights on at 7.00 am and lights off at 19.00 pm. Locomotor activity was measured using AUTOMEX II activity monitors (Columbus Instruments, Columbus, Ohio, USA). Fifteen minutes before administration of either 0.5 mg/kg or 2 mg/kg D-amphetamine (Sigma, St. Louis, Mo., USA), experimental drugs were administered s.c. in a volume of 1 mL/kg. Drugs were dissolved in saline. After administering 0.5 mg/kg D-amphetamine, rats were placed in plexiglas cages mounted on the activity monitors and, after a 5 min waiting period, measurements were started. Activity was recorded for 60 min in 15 min intervals.

| Inhibition of D-Amphetamine induced hypermotility (acc. counts/h ± SEM); n = 4 | |
|---|---|
| 22 (10 µmol/kg sc) + D-AMPH 0.5 mg/kg | 570 ± 230 (18% of contr.) |
| saline + D-AMPH 0.5 mg/kg | 3180 ± 850 |

Contralateral Rotations in Unilaterally Lesioned Marmosets Animals

Six common marmosets (Callitrix Jacchus, three females and three males) weighing 270–450 grams each were used in the study. The animals were housed in pairs of two, all in a temperature-controlled (25±1° C.) and a humidity (relative 50%) controlled environment with a 12 hour. day-night cycle (lightning was on from 6 am. to 6 p.m.). The marmosets received fortified milk solution with bread in the mornings and fresh fruit in the afternoons. The monkeys had free access to water at all times.

The study was approved by the Animal Ethics Committee, Uppsala University.

6OHDA lesion

The animals were placed in a Kopf stereotaxic instrument under ketamine 80 mg/kg (Ketalar®, 50 mg/ml, Parke-Davis) and xylazine 4.5 mg/kg (Rompur® vet. 20 mg/ml Bayer AG) anesthesia. Prior to anesthesia induction they were pretreated with desipramine (25 mg/kg i.m.). Aseptic conditions were maintained during surgery. 6-OHDA HBr with ascorbic acid (Research Bio-chemicals Inc., Natick, Mass.) was dissolved in saline to a concentration of 4 mg/ml and intracerebrally injected into five sites of the nigrostriatal bundle according to the method reported by Annet et al., (1992). The brain coordinates were as follows from the neural atlas of Stephan et al., (1980): Anterior-posterior (AP) +6.5, medial-lateral (ML) −1.2, dorsal-ventral (DV) +7.0. DV +6.0, ML −2.2, DV +7.5, DV +6.5, ML −3.2, DV +7.5. The toxin was injected on the right side of the brain with 2 µl injected into all sites except for the most medial site where 3 µl were injected. The animals quickly recovered from surgery.

The experiments were started at least 16 months after the intracerebral injections. Two weeks before the start of the experiments the animals were tested for responsiveness to apomorphine. Apomorphine HCL (Apomorphini hydrochloridum ½ AQ, Apoteksbolaget) was dissolved in sterile water in a concentration of 0.15 mg/ml. The animals were put individually into an aluminum observation cage (46.5× 46.5×62 cm) with stainless steel grid doors (46.6×62 cm) and observed for 60 minutes after a subcutaneous apomorphine injection at the dose of 0.2 mg/kg subcutaneously (s.c.). Only animals showing contralateral rotations in response to apomorphine were used in subsequent tests.

Drugs

The monkeys had been part of other drug protocols previous to this experiment. However, they were kept drug-free for at least one month before the start of the present protocol. All drug solutions used in the study were prepared the day for the experiments and only one experiment was performed on each monkey each week.

Dopaminomimetics: Apomorphine HCL (Apomorphini hydrochloridum ½ AQ, Apoteksbolaget) was dissolved in sterile water in a concentration of 0.2 mg/kg and was administered s.c. in the neck for the experiments.

Compound 22 was given in three different doses s.c. in the neck to each monkey (0.3, 1.0 and 3.0 mg/kg). Compound 22 was prepared with 0.9% saline at the day for the experiment. Compound 22 was administered s.c. in the neck together with apomorphine or alone.

Behavioral Assessments (Turning Behavior)

Behavioral assessments were all conducted in a separate observation cage. This measured 62×46.5×46.5 cm, and had stainless steel bars in the front. After each drug administration ipsi- and contralateral turns were counted by visual inspection every minutes for 60 minutes. For the scoring, only sill turns were counted. An initial period of 10 minutes was permitted for habituation to the cage before drug dosing and observation.

Statistical Analysis

Data were analyzed using a one-way analysis of variance (ANOVA) with repeated measurements. In cases where the resulting F values where associated with $p<0.05$, groups were compared using a paired t-test The accepted level of significance was $p<0.05$.

Table 1. Contralateral rotation, as induced by compound 22, with or without pre-treatment with 0.2 mg/kg of Apomorphine. Doses of compound 22 are given in mg/kg in parentheses).

| Marmoset number | weight gram | NaCl Apo | 22 (0.3) NaCl | 22 (0.3) Apo | 22 (1.0) NaCl | 22 (1.0) Apo | 22 (3.0) NaCl | 22 (3.0) Apo |
|---|---|---|---|---|---|---|---|---|
| 4 (D24) | 460 | 218 | 0 | 157 | 0 | 0 | 0 | 0 |
| 50 (Z9) | 380 | 472 | 0 | 0 | 0 | 0 | 0 | 0 |
| 30 (D14) | 430 | 762 | 0 | 0 | 0 | 11 | 0 | 0 |
| 21 (D21) | 290 | 1114 | 0 | 1179 | 34 | 1825 | 0 | 1349 |
| 21 (D21) | 290 | — | — | — | — | 1242 | — | — |
| 61 (F8) | 340 | 1144 | 58 | 1494 | 223 | 1396 | 57 | 1805 |
| 35 (F3) | 256 | 1344 | 41 | 1194 | 92 | 815 | 15 | 909 |

Ipsilateral Rotations in Unilaterally Lesioned Marmosets

The 6-OH-DA lesioned marmosets may also be pretreated with a suitable dose of (+)-Amphetamine to induce a certain degree of ipsilateral turning. This effect may be influenced by some compounds of the present invention. The concept being that the intact DA neurones on the non-lesioned side will release DA on a challenge from the dose of (+)-Amphetamine administered. The DA released will reach the normosensitive postsynaptic DA receptors of these neuronal systems and induce a behavior of ipsilateral turning, which is likely to be less intense than the contralateral rotation induced by DA agonists (like the full agonist Apomorphine), since the DA receptors on the lesioned side are much more sensitive than those on the non-lesioned side. Manual scoring is applied to quantify such ipsilateral turning behavior.

MPTP Treated Rhesus Monkeys: A Model for Parkinson's Disease

The discovery of the neurotoxin 1-methyl-4-phenyl-1,2,3,6-tetrahydropyridine (MPTP) (Langston et al., Science 219, 979 (1983)) provided an animal model for Parkinson's disease. The irreversible neurological syndrome triggered by MPTP in man and in monkeys largely resembles the idiopathic Parkinson's disease in its clinical, pathological, biochemical and pharmacological characteristics (Markey et al., Nature 311, 464 (1984)). The reason for this convincing similarity is the fact that MPTP selectively destroys the small group of dopaminergic nerve cells in the substantia nigra of the brain which are also destroyed by degenerative processes in naturally occurring Parkinson's disease. There is even some talk that the cause of idiopathic Parkinson's disease is MPTP or a similar compound forming in the organism (Snyder, S. H., Nature 311, 514 (1984)). Possibly as a result of the specific metabolism of MPTP, the clinical impression of the MPTP-Parkinson picture has hitherto been demonstrated only in monkeys and man. The MPTP model realized in Rhesus monkeys is, therefore, exceptionally suitable for testing the activity of anti-Parkinson's disease drugs. Some of the compounds of the present invention have potential anti-Parkinson effects.

MPTP Treated Marmosets: A Model for Parkinson's Disease

Another such model is represented by the male common marmosets (Ekesbo et al. Neuroreport 1997, 8, 2567–2570). The male common marmosets (body weights 350–385 g at the time of the experiments) are housed in a common cage with a temperature (26±1° C.) and humidity (relative 50%) controlled environment and a 12:12 h light/dark cycle (lights on 06.00–18.00 h). The monkeys have free access to water and fresh orange juice and once a day they are given gruel with bread. All animals are treated for 5 days with MPTP× HCl (2.0 mg/kg/day dissolved in 0.9% saline, s.c.) in a single daily injection. After MPTP treatment for 3 consecutive days, a 2-day break is allowed for the animals to regain body fluid. After the fifth day of MPTP treatment, a severe PD-like syndrome with akinesia, bradykinesia and rigidity develops. The degree of motor dysfunction is scored on a visual disability grading system, including the following items: alertness; reaction to stimuli; checking movements; attention and eye movements; posture; balance; motility; vocalization and tremor. The disability score for each animal is rated every morning for each monkey.

MPTP Treated Marmosets: L-DOPA/Carbidopa-induced Dyskinesias

Levodopa/caibidopa (15/7.5 mg/kg, twice daily) is started the day after the last MPTP×HCl injection and continued throughout the study. The levodopa solution is freshly prepared in saline containing 5%, glucose to a levodopa/carbidopa concentration of 1.6/0.8 mg/ml and is administered i.p. After levodopa injection, a reversal of Parkinsonian features is seen within 5–10 min in all animals. Following normalization of posture, there is a marked increase mobility and increased vocalization. All animals seem unusually restless and appear to be driven to move. Climbing is prominent, both vertically and horizontally in the cages on all four walls as well as up-side-down climbing on the ceiling, often along with stereotyped tapping or touching of the cage bars and walls.

Peak dose dyskinetic movements appears in the test animals after 8–10 days of levodopa treatment and gradually become more severe and generalized during the following days. Two weeks after levodopa initialization each animal shows an idiosyncratic pattern of dyskinesias which are highly reproducible. These dyskinetic movements are apparent shortly after induction of the anti-parkinsonian effect and consist of intense arm dyskinesias with bilateral reaching, waving and distal flicking movements. Hindlimb chorea and hemichoretic ballism are occasionally seen. Dystonic movements are sparse but when present they occur before, during and after levodopa dosing. Dystonia is usually present in the form of neck dystonia with sustained retrocollis. The degrees of dyskinetic and motor dysfunction is evaluated by visual inspection, on-site, as well as by the subsequent inspection of video tapes for each animal and for each of the drugs and doses tested. The presence of dyskinesias is scored with a specifically designed dyskinesia scoring system.

All ratings are made by trained observers.

Models to Test for Potential Effects Against Drug Abuse

Recently, many studies have indicated that the interaction of ethanol with dopamine transmission within the limbic system of the basal forebrain may be of particular functional importance concerning ethanol reinforcement. Especially, electrophysiological studies indicated that systematic administration of ethanol in rats selectively stimulates the firing of dopamine-containing cells of the ventral segmental area (VTA) projecting to the nucleus accumbens (Pulvirenti L, Koob GF, 1994, Dopamine agonists, partial agonists and psychostimulant addiction, Trends Pharmacol. Sci. 15, 374–379). Bono et al. have found that both acute and chronic administration of partial dopamine agonists significantly reduced the ethanol intake (Bono G, Balducci C, Richelmi P, Koob G F, Pulvirenti L, 1996, Dopamine partial receptor agonists reduce ethanol intake in rat Eur. J. Pharmacol 296, 233–238). It has been suggested that dopamine partial receptor agonists reduce the reinforcing properties of ethanol in the rat, an effect similar to that previously observed with cocaine. The partial agonists used in the study of Pulvirenti and Koob (Bono G, Balducci C, Richelmi P, Koob G F, Pulvirenti L, 1996, Dopamine partial receptor agonists reduce ethanol intake in rat Eur. J. Pharmacol 296, 233–238) bind to the dopamine receptor with high affinity but low intrinsic activity. The functional consequence is that these compounds act as antagonists under conditions of high dopaminergic tone. In conditions of low dopamine tone, as after denervation or during functional depletion of the neurotransmitter, partial receptor agonists show agonistic properties. Compounds of the present invention may show an effect in pharmacological models for inhibition of drug abuse (see below) and may be potential clinical agents for such conditions.

Materials and Methods

Male albino Wistar rats (Charles River) weighing 100–120 g at the beginning of training, are housed individually and exposed to a normal 12-h light-dark cycle (lights on 7:00 am.–7:00 p.m.). Rats are initially water deprived for 3 days only (22 h/day) to motivate drinking during the 2 h of daily exposure to ethanol. Food and water are then available ad libitum throughout subsequent training and testing periods. All training and testing is conducted in the home cages. Animals are trained to drink ethanol using a variant of the sucrose fading technique previously described by Samson (1986) and modified by Rassnick et al. (1992). In the present study, saccharin is added to the ethanol solution to increase the palatability of the ethanol solution and to overcome ethanol's aversive taste. Initially rats are trained for 3 days in 120 min daily sessions to drink from either of two bottles containing water or 0.2% (w/v) saccharin reinforcement. Then rats are exposed daily for 120 min to a free-choice condition where one bottle contains water, the other 0.2% (w/v) saccharin+ethanol, with the ethanol side alternated daily. During training days 4–10 rats are trained to drink from either of two bottles containing water or ethanol 5% (w/y)+saccharin 0.2% (w/v). On training days 10–12 rats are given access to two bottles containing water or ethanol 5% (w/v). Thereafter, the concentration of ethanol is increased to 8% with 3 days of access to an ethanol-saccharin solution and 1 day of access to 8% ethanol without saccharin. Ethanol at 10% is then introduced in the presence of saccharin and training to respond for this concentration is conducted for 3 days. The concentration of saccharin is then gradually faded out and animals are exposed daily to 10% ethanol or water free-choice procedure in the absence of water or food deprivation and without sweeteners in the ethanol solution. The entire training period generally requires 20–30 days. At the end of the training, a stable baseline intake is reached, defined as ±20% of intake for 3 consecutive days. All training and testing sessions consists of 120-min daily sessions conducted between 9:00 a.m. and 12:00 p.m. Ethanol solutions are prepared from 100% ethyl alcohol and diluted with tap water for concentrations of 5, 8 and 10% (w/v).

Radical Scavenging Properties

The compounds of the present invention may possess radical scavenging/anti-oxidant properties, which can be investigated with the (non-enzymatic) lipid peroxidation assay. In this assay, radical formation through the Fenton reaction is induced by adding $Fe^{2+}$ and ascorbate to a preparation of rat liver microsomes. These radicals initiate a process called lipid peroxidation, which may be inhibited by a radical scavenger (Haenen and Bast, FEBS Lett. 1983, 159, 24–28).

What is claimed is:

1. 2-Aminothiazol-fused 2-aminoindans and 2-aminotetralins having the general Formula 1:

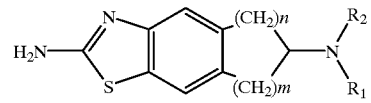

wherein
$R_1$ and $R_2$, which may be identical or different, are selected from the group consisting of a hydrogen atom, alkyl or haloalkyl groups of 1 to 7 carbon atoms, (alkyl)cycloalkyl groups of 3 to 7 carbon atoms, alkenyl or alkynyl groups of 3 to 6 carbon atoms, and arylalkyl having 1 to 3 carbon atoms in the alkyl moiety, whilst the aryl nucleus may be substituted; and
n and m are 1 or 2,
or an enantiomer or acid addition salt thereof.

2. 2-Aminothiazol-fused 2-aminoindans according to claim 1, which have the general Formula 1a:

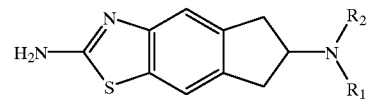

wherein $R_1$ and $R_2$ are as defined in claim 1, or acid addition salt thereof.

3. 2-Aminothiazol-fused 2-aminoindans according to claim 2, wherein $R_1$ is n-propyl and $R_2$ is H, $(C_1-C_7)$alkyl or halo$(C_1-C_7)$alkyl, or an enantiomer or an acid addition salt thereof.

4. 2-Aminothiazol-fused 2-aminoindans according to claim 2, wherein $R_1$ is n-propyl and $R_2$ is aryl-ethyl or an enantiomer or an acid addition salt thereof.

5. 2-Aminothiazol-fused 2-aminotetralins according to claim 1, which have the general Formula 1b:

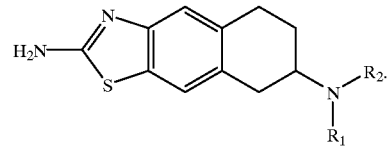

6. 2-Aminothiazol-fused 2-aminotetralins according to claim 1, which have the general Formula 1c:

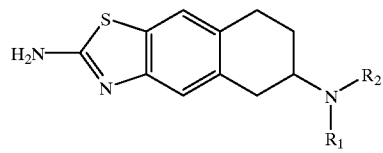

wherein $R_1$ and $R_2$ are as defined in claim 1, or an acid addition salt thereof.

7. 2-Aminothiazol-fused 2-aminotetralins according to claim 5 wherein $R_1$ is n-propyl and $R_2$ is H, $(C_1-C_7)$alkyl or halo$(C_1-C_7)$alkyl or an enantiomer or an acid addition salt thereof.

8. 2-Aminothiazol-fused 2-aminotetralins according to claim 5, wherein $R_1$ is n-propyl and $R_2$ is aryl-ethyl or an enantiomer or an acid addition salt thereof.

9. Compounds according to claim 1, wherein the acid addition salts are physiologically acceptable acid addition salts with inorganic or organic acids.

10. Pharmaceutical compositions containing as active substance a compound as claimed in claim 1 or a physiologically acceptable acid addition salt thereof optionally together with one or more inert carriers and/or diluents.

11. Processing for preparing a pharmaceutical composition, characterized in that a compound as claimed in claim 1 or a physiologically acceptable acid addition salt thereof is incorporated in one or more inert carriers and/or diluents by a non-chemical method.

12. 2-Aminothiazol-fused 2-aminoindans according to claim 2, wherein $R_1$ is n-propyl and $R_2$ is n-propyl; or an acid addition salt thereof.

13. 2-Aminothiazol-fused 2-aminoindans according to claim 2, wherein $R_1$ is n-propyl and $R_2$ is 2-thienylethyl; or an enantiomer or an acid addition salt thereof.

14. 2-Aminothiazol-fused 2-aminotetralins according to claim 6, wherein $R_1$ is n-propyl and $R_2$ is H, $(C_1-C_7)$alkyl or halo $(C_1-C_7)$alkyl; or an enantiomer or an acid addition salt thereof.

15. 2-Aminothiazol-fused 2-aminotetralins according to claim 5, wherein $R_1$ is n-propyl and $R_2$ is n-propyl; or an acid addition salt thereof.

16. 2-Aminothiazol-fused 2-aminotetralins according to claim 6, wherein $R_1$ is n-propyl and $R_2$ is n-propyl; or an acid addition salt thereof.

17. 2-Aminothiazol-fused 2-aminotetralins according to claim 5, wherein $R_1$ is n-propyl and $R_2$ is 2-thienyethyl; or an enantiomer or an acid addition salt thereof.

18. 2-Aminothiazol-fused 2-aminotetralins accordinf to claim 6, wherein $R_1$ is n-propyl and $R_2$ is 2-thienylethyl; or an enantiomer or an acid addition salt thereof.

* * * * *